United States Patent
Vaccarella et al.

(10) Patent No.: US 11,717,323 B2
(45) Date of Patent: *Aug. 8, 2023

(54) SEALS FOR SURGICAL ACCESS DEVICES

(71) Applicant: Covidien LP, Mansfield, MA (US)

(72) Inventors: Lorenzo Vaccarella, Bellingham, MA (US); Garrett Ebersole, Hamden, CT (US); Robert Pedros, Oxford, CT (US)

(73) Assignee: Covidien LP, Mansfield, MA (US)

( * ) Notice: Subject to any disclaimer, the term of this patent is extended or adjusted under 35 U.S.C. 154(b) by 162 days.

This patent is subject to a terminal disclaimer.

(21) Appl. No.: 17/317,014

(22) Filed: May 11, 2021

(65) Prior Publication Data

US 2021/0259734 A1    Aug. 26, 2021

Related U.S. Application Data

(63) Continuation of application No. 16/394,043, filed on Apr. 25, 2019, now Pat. No. 11,000,313.

(51) Int. Cl.
  *A61B 17/34*  (2006.01)
  *A61M 13/00*  (2006.01)

(52) U.S. Cl.
  CPC ...... *A61B 17/3439* (2013.01); *A61B 17/3423* (2013.01); *A61B 17/3498* (2013.01);
  (Continued)

(58) Field of Classification Search
  CPC . A61B 17/34; A61B 17/3462; A61B 17/3421; A61B 17/3423; A61B 17/3494; A61B 17/3498; A61B 2017/3464
  (Continued)

(56) References Cited

U.S. PATENT DOCUMENTS

| 3,402,710 A | 9/1968 | Paleschuck |
| 3,495,586 A | 2/1970 | Regenbogen |

(Continued)

FOREIGN PATENT DOCUMENTS

| CA | 2702419 A1 | 11/2010 |
| EP | 0226026 A2 | 6/1987 |

(Continued)

OTHER PUBLICATIONS

European Search Report dated Aug. 25, 2020, issued in EP Appln. No. 20171223, 7 pages.

*Primary Examiner* — Eduardo C Robert
*Assistant Examiner* — Christina Negrellirodriguez
(74) *Attorney, Agent, or Firm* — Carter, DeLuca & Farrell LLP

(57) ABSTRACT

A cannula for use in an access assembly includes an instrument valve housing including first and second housing sections and defining a cavity and a valve assembly disposed within the cavity of the instrument valve housing. The valve assembly includes a seal assembly including an outer flange and a septum seal extending across the outer flange, a guard assembly disposed within the outer flange of the seal assembly, and a centering mechanism. The guard assembly includes a plurality of guard members. Each guard member of the plurality of guard members includes a ring portion and a flap portion. The flap portions of the guard members of the guard assembly are configured to engage and stretch the septum seal during reception of a surgical instrument through the valve assembly.

19 Claims, 8 Drawing Sheets

(52) U.S. Cl.
CPC .............. *A61B 2017/3419* (2013.01); *A61B 2017/3464* (2013.01); *A61M 13/00* (2013.01)

(58) Field of Classification Search
USPC ........................................................ 600/208
See application file for complete search history.

(56) References Cited

U.S. PATENT DOCUMENTS

| | | |
|---|---|---|
| 4,016,884 A | 4/1977 | Kwan-Gett |
| 4,112,932 A | 9/1978 | Chiulli |
| 4,183,357 A | 1/1980 | Bentley et al. |
| 4,356,826 A | 11/1982 | Kubota |
| 4,402,683 A | 9/1983 | Kopman |
| 4,653,476 A | 3/1987 | Bonnet |
| 4,737,148 A | 4/1988 | Blake |
| 4,863,430 A | 9/1989 | Klyce et al. |
| 4,863,438 A | 9/1989 | Gauderer et al. |
| 4,984,564 A | 1/1991 | Yuen |
| 5,002,557 A | 3/1991 | Hasson |
| 5,073,169 A | 12/1991 | Raiken |
| 5,082,005 A | 1/1992 | Kaldany |
| 5,122,122 A | 6/1992 | Allgood |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,209,741 A | 5/1993 | Spaeth |
| 5,209,754 A | 5/1993 | Ahluwalia |
| 5,217,466 A | 6/1993 | Hasson |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |
| 5,290,249 A | 3/1994 | Foster et al. |
| 5,312,391 A | 5/1994 | Wilk |
| 5,312,417 A | 5/1994 | Wilk |
| 5,314,417 A | 5/1994 | Stephens et al. |
| 5,318,516 A | 6/1994 | Cosmescu |
| 5,330,486 A | 7/1994 | Wilk |
| 5,334,143 A | 8/1994 | Carroll |
| 5,336,169 A | 8/1994 | Divilio et al. |
| 5,336,203 A | 8/1994 | Goldhardt et al. |
| 5,337,937 A | 8/1994 | Remiszewski et al. |
| 5,345,927 A | 9/1994 | Bonutti |
| 5,360,417 A | 11/1994 | Gravener et al. |
| 5,366,478 A | 11/1994 | Brinkerhoff et al. |
| 5,375,588 A | 12/1994 | Yoon |
| 5,378,588 A | 1/1995 | Tsuchiya |
| 5,391,156 A | 2/1995 | Hildwein et al. |
| 5,394,863 A | 3/1995 | Sanford et al. |
| 5,395,367 A | 3/1995 | Wilk |
| 5,437,683 A | 8/1995 | Neumann et al. |
| 5,445,615 A | 8/1995 | Yoon |
| 5,451,222 A | 9/1995 | De Maagd et al. |
| 5,460,170 A | 10/1995 | Hammerslag |
| 5,464,409 A | 11/1995 | Mohajer |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,520,698 A | 5/1996 | Koh |
| 5,522,791 A | 6/1996 | Leyva |
| 5,524,644 A | 6/1996 | Crook |
| 5,540,648 A | 7/1996 | Yoon |
| 5,545,150 A | 8/1996 | Danks et al. |
| 5,545,179 A | 8/1996 | Williamson, IV |
| 5,556,385 A | 9/1996 | Andersen |
| 5,569,159 A | 10/1996 | Anderson et al. |
| 5,577,993 A | 11/1996 | Zhu et al. |
| 5,601,581 A | 2/1997 | Fogarty et al. |
| 5,624,399 A | 4/1997 | Ackerman |
| 5,634,911 A | 6/1997 | Hermann et al. |
| 5,634,937 A | 6/1997 | Mollenauer et al. |
| 5,643,285 A | 7/1997 | Rowden et al. |
| 5,649,550 A | 7/1997 | Crook |
| 5,651,771 A | 7/1997 | Fangherlini et al. |
| 5,653,705 A | 8/1997 | de la Torre et al. |
| 5,656,013 A | 8/1997 | Yoon |
| 5,672,168 A | 9/1997 | de la Torre et al. |
| 5,683,378 A | 11/1997 | Christy |
| 5,685,857 A | 11/1997 | Negus et al. |
| 5,697,946 A | 12/1997 | Hopper et al. |
| 5,709,675 A | 1/1998 | Williams |
| 5,713,858 A | 2/1998 | Heruth et al. |
| 5,713,869 A | 2/1998 | Morejon |
| 5,722,962 A | 3/1998 | Garcia |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,752,970 A | 5/1998 | Yoon |
| 5,782,817 A | 7/1998 | Franzel et al. |
| 5,795,290 A | 8/1998 | Bridges |
| 5,803,921 A | 9/1998 | Bonadio |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,836,913 A | 11/1998 | Orth et al. |
| 5,840,077 A | 11/1998 | Rowden et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,817 A | 2/1999 | Moenning et al. |
| 5,871,474 A | 2/1999 | Hermann et al. |
| 5,876,413 A | 3/1999 | Fogarty et al. |
| 5,894,843 A | 4/1999 | Benetti et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,914,415 A | 6/1999 | Tago |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,964,781 A | 10/1999 | Mollenauer et al. |
| 5,976,174 A | 11/1999 | Ruiz |
| 5,997,515 A | 12/1999 | de la Torre et al. |
| 6,017,355 A | 1/2000 | Hessel et al. |
| 6,018,094 A | 1/2000 | Fox |
| 6,024,736 A | 2/2000 | de la Torre et al. |
| 6,030,402 A | 2/2000 | Thompson et al. |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |
| 6,099,506 A | 8/2000 | Macoviak et al. |
| 6,110,154 A | 8/2000 | Shimomura et al. |
| 6,142,936 A | 11/2000 | Beane et al. |
| 6,156,006 A | 12/2000 | Brosens et al. |
| 6,162,196 A | 12/2000 | Hart et al. |
| 6,171,282 B1 | 1/2001 | Ragsdale |
| 6,197,002 B1 | 3/2001 | Peterson |
| 6,217,555 B1 | 4/2001 | Hart et al. |
| 6,228,063 B1 | 5/2001 | Aboul-Hosn |
| 6,234,958 B1 | 5/2001 | Snoke et al. |
| 6,238,373 B1 | 5/2001 | de la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | de la Torre et al. |
| 6,319,246 B1 | 11/2001 | de la Torre et al. |

(56) References Cited

U.S. PATENT DOCUMENTS

| | | |
|---|---|---|
| 6,328,720 B1 | 12/2001 | McNally et al. |
| 6,329,637 B1 | 12/2001 | Hembree et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,485,410 B1 | 11/2002 | Loy |
| 6,488,620 B1 | 12/2002 | Segermark et al. |
| 6,488,692 B1 | 12/2002 | Spence et al. |
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,558,371 B2 | 5/2003 | Dorn |
| 6,562,022 B2 | 5/2003 | Hoste et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Lezdey |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,753,901 B2 | 7/2010 | Piskun et al. |
| 7,758,500 B2 | 7/2010 | Boyd et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,951,076 B2 | 5/2011 | Hart et al. |
| 7,955,257 B2 | 6/2011 | Frasier et al. |
| 7,955,313 B2 | 6/2011 | Boismier |
| 7,998,068 B2 | 8/2011 | Bonadio et al. |
| 3,021,296 A1 | 9/2011 | Bonadio et al. |
| 3,025,670 A1 | 9/2011 | Sharp et al. |
| 8,038,652 B2 | 10/2011 | Morrison et al. |
| 8,066,673 B2 | 11/2011 | Hart et al. |
| 8,079,986 B2 | 12/2011 | Taylor et al. |
| 8,092,430 B2 | 1/2012 | Richard et al. |
| 8,105,234 B2 | 1/2012 | Ewers et al. |
| 8,109,873 B2 | 2/2012 | Albrecht et al. |
| 8,157,786 B2 | 4/2012 | Miller et al. |
| 8,157,817 B2 | 4/2012 | Bonadio et al. |
| 8,187,177 B2 | 5/2012 | Kahle et al. |

(56) References Cited

U.S. PATENT DOCUMENTS

| | | |
|---|---|---|
| 8,187,178 B2 | 5/2012 | Bonadio et al. |
| 8,241,209 B2 | 8/2012 | Shelton, IV et al. |
| 8,262,568 B2 | 9/2012 | Albrecht et al. |
| 8,323,184 B2 | 12/2012 | Spiegal et al. |
| 8,335,783 B2 | 12/2012 | Milby |
| 8,343,047 B2 | 1/2013 | Mbrecht et al. |
| 8,353,824 B2 | 1/2013 | Shelton, IV et al. |
| 8,403,889 B2 | 3/2013 | Richard |
| 8,480,683 B2 | 7/2013 | Fowler et al. |
| 8,574,153 B2 | 11/2013 | Richard |
| 8,585,632 B2 | 11/2013 | Okoniewski |
| 11,000,313 B2 * | 5/2021 | Vaccarella ......... A61B 17/3423 |
| 2001/0037053 A1 | 11/2001 | Bonadio et al. |
| 2002/0055714 A1 | 5/2002 | Rothschild |
| 2003/0014076 A1 | 1/2003 | Mollenauer et al. |
| 2003/0093104 A1 | 5/2003 | Bonner et al. |
| 2003/0187376 A1 | 10/2003 | Rambo |
| 2003/0233115 A1 | 12/2003 | Eversull et al. |
| 2003/0236549 A1 | 12/2003 | Bonadio et al. |
| 2004/0059297 A1 | 3/2004 | Racenet et al. |
| 2004/0092795 A1 | 5/2004 | Bonadio et al. |
| 2004/0102804 A1 | 5/2004 | Chin |
| 2004/0111061 A1 | 6/2004 | Curran |
| 2004/0138529 A1 | 7/2004 | Wiltshire et al. |
| 2004/0204734 A1 | 10/2004 | Wagner et al. |
| 2004/0267096 A1 | 12/2004 | Caldwell et al. |
| 2005/0020884 A1 | 1/2005 | Hart et al. |
| 2005/0070935 A1 | 3/2005 | Ortiz |
| 2005/0096695 A1 | 5/2005 | Olich |
| 2005/0119525 A1 | 6/2005 | Takemoto |
| 2005/0137459 A1 | 6/2005 | Chin et al. |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0209608 A1 | 9/2005 | O'Heeron |
| 2005/0245876 A1 | 11/2005 | Khosravi et al. |
| 2005/0251092 A1 | 11/2005 | Howell et al. |
| 2005/0277946 A1 | 12/2005 | Greenhalgh |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0212063 A1 | 9/2006 | Wilk |
| 2006/0224161 A1 | 10/2006 | Bhattacharyya |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0203398 A1 | 8/2007 | Bonadio et al. |
| 2007/0208312 A1 | 9/2007 | Norton et al. |
| 2007/0225650 A1 | 9/2007 | Hart et al. |
| 2007/0270654 A1 | 11/2007 | Pignato et al. |
| 2007/0270882 A1 | 11/2007 | Hjelle et al. |
| 2008/0009826 A1 | 1/2008 | Miller et al. |
| 2008/0021360 A1 | 1/2008 | Fihe et al. |
| 2008/0027476 A1 | 1/2008 | Piskun |
| 2008/0048011 A1 | 2/2008 | Weller |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0161826 A1 | 7/2008 | Guiraudon |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0255519 A1 | 10/2008 | Piskun et al. |
| 2008/0319261 A1 | 12/2008 | Lucini et al. |
| 2009/0012477 A1 | 1/2009 | Norton et al. |
| 2009/0036738 A1 | 2/2009 | Cuschieri et al. |
| 2009/0036745 A1 | 2/2009 | Bonadio et al. |
| 2009/0093752 A1 | 4/2009 | Richard et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0326330 A1 | 12/2009 | Bonadio et al. |
| 2009/0326332 A1 | 12/2009 | Carter |
| 2010/0063452 A1 | 3/2010 | Edelman et al. |
| 2010/0100043 A1 | 4/2010 | Racenet |
| 2010/0113886 A1 | 5/2010 | Piskun et al. |
| 2010/0228094 A1 | 9/2010 | Ortiz et al. |
| 2010/0240960 A1 | 9/2010 | Richard |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0298646 A1 | 11/2010 | Stellon et al. |
| 2010/0312063 A1 | 12/2010 | Hess et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0118553 A1 | 5/2011 | Stopek |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0313250 A1 | 12/2011 | Kleyman |
| 2012/0059640 A1 | 3/2012 | Roy et al. |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |
| 2012/0190933 A1 | 7/2012 | Kleyman |
| 2012/0209077 A1 | 8/2012 | Racenet |

(56) References Cited

U.S. PATENT DOCUMENTS

| | | |
|---|---|---|
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0283520 A1 | 11/2012 | Kleyman |
| 2013/0225930 A1 | 8/2013 | Smith |
| 2013/0225931 A1 | 8/2013 | Cruz et al. |
| 2013/0245373 A1 | 9/2013 | Okoniewski |
| 2013/0274559 A1 | 10/2013 | Fowler et al. |
| 2013/0310651 A1 | 11/2013 | Alfieri |
| 2014/0018632 A1 | 1/2014 | Kleyman |
| 2018/0021063 A1 | 1/2018 | Main et al. |
| 2019/0059938 A1 | 2/2019 | Holsten |

FOREIGN PATENT DOCUMENTS

| | | |
|---|---|---|
| EP | 0538060 A1 | 4/1993 |
| EP | 0577400 A1 | 1/1994 |
| EP | 0630660 A1 | 12/1994 |
| EP | 0807416 A2 | 11/1997 |
| EP | 0950376 A1 | 10/1999 |
| EP | 1188415 A2 | 3/2002 |
| EP | 1312318 A1 | 5/2003 |
| EP | 1774918 A1 | 4/2007 |
| EP | 1932485 A1 | 6/2008 |
| EP | 2044889 A1 | 4/2009 |
| EP | 2044897 A1 | 4/2009 |
| EP | 2080494 A1 | 7/2009 |
| EP | 2095781 A2 | 9/2009 |
| EP | 2098182 A2 | 9/2009 |
| EP | 2138117 A1 | 12/2009 |
| EP | 2138118 A2 | 12/2009 |
| EP | 2181657 A2 | 5/2010 |
| EP | 2226025 A1 | 9/2010 |
| EP | 2229900 A1 | 9/2010 |
| EP | 2238924 A1 | 10/2010 |
| EP | 2238925 A1 | 10/2010 |
| EP | 2238926 A2 | 10/2010 |
| EP | 2238933 A1 | 10/2010 |
| EP | 2248478 A1 | 11/2010 |
| EP | 2248482 A1 | 11/2010 |
| EP | 2253283 A1 | 11/2010 |
| EP | 2272450 A2 | 1/2011 |
| EP | 2277464 A1 | 1/2011 |
| EP | 2289438 A1 | 3/2011 |
| EP | 2292165 A2 | 3/2011 |
| EP | 2343019 | 7/2011 |
| GB | 2469083 | 4/2009 |
| WO | 84/01512 A1 | 4/1984 |
| WO | 9314801 A1 | 8/1993 |
| WO | 9404067 A1 | 3/1994 |
| WO | 9610963 A1 | 4/1996 |
| WO | 9636283 A1 | 11/1996 |
| WO | 9733520 A1 | 9/1997 |
| WO | 9742889 A1 | 11/1997 |
| WO | 9916368 | 4/1999 |
| WO | 9922804 | 5/1999 |
| WO | 9929250 | 6/1999 |
| WO | 0032116 | 6/2000 |
| WO | 0032120 | 6/2000 |
| WO | 0054675 | 9/2000 |
| WO | 0108581 A2 | 2/2001 |
| WO | 0149363 A1 | 7/2001 |
| WO | 0207611 A2 | 1/2002 |
| WO | 03034908 A2 | 5/2003 |
| WO | 03071926 | 9/2003 |
| WO | 03077726 | 9/2003 |
| WO | 2004043275 A1 | 5/2004 |
| WO | 2004054456 A1 | 7/2004 |
| WO | 2004075741 A2 | 9/2004 |
| WO | 2004075930 A2 | 9/2004 |
| WO | 2005058409 A1 | 6/2005 |
| WO | 2006019723 | 2/2006 |
| WO | 2006100658 A2 | 9/2006 |
| WO | 2006110733 A2 | 10/2006 |
| WO | 2007018458 | 2/2007 |
| WO | 2007095703 | 8/2007 |
| WO | 2007143200 | 12/2007 |
| WO | 2008015566 A2 | 2/2008 |
| WO | 2008042005 | 4/2008 |
| WO | 2008077080 A2 | 6/2008 |
| WO | 2008093313 | 8/2008 |
| WO | 2008103151 A2 | 8/2008 |
| WO | 2008121294 A1 | 10/2008 |
| WO | 2008147644 | 12/2008 |
| WO | 2009036343 A1 | 3/2009 |
| WO | 2010000047 | 1/2010 |
| WO | 2010141409 A1 | 12/2010 |
| WO | 2010141673 A1 | 12/2010 |

* cited by examiner

SEALS FOR SURGICAL ACCESS DEVICES

CROSS REFERENCE TO RELATED APPLICATION

This application is a continuation of U.S. patent application Ser. No. 16/394,043, filed Apr. 25, 2019, the entire contents of each of which is hereby incorporated by reference herein.

BACKGROUND

Technical Field

The present disclosure relates to seals. More particularly, the present disclosure relates to seals for surgical access devices.

Background

In order to facilitate minimally invasive surgery, a working space must be created in the desired surgical plane. An injection of an insufflation fluid, typically $CO_2$, can be used to create a pneumoperitoneum in the abdomen. To work in the created space, access ports are required for surgical instrumentation and cameras. These ports maintain the pressure creating the pneumoperitoneum with seals that adapt to the surgical instrumentation.

The breadth of surgical instrumentation on the market today requires a robust seal capable adjusting to multiple sizes and withstanding multiple insertions of surgical instrumentation. Therefore, it would be beneficial to have an access assembly with improved seal durability.

SUMMARY

A cannula for use in an access assembly is provided. The cannula includes an instrument valve housing including first and second housing sections and defining a cavity and a valve assembly disposed within the cavity of the instrument valve housing. The valve assembly includes a seal assembly including an outer flange and a septum seal extending across the outer flange, a guard assembly disposed within the outer flange of the seal assembly, and a centering mechanism including an annular ring and a plurality of spokes extending outwardly from the annular ring. The guard assembly includes a plurality of guard members. Each guard member of the plurality of guard members includes a ring portion and a flap portion. The outer flange of the seal assembly is supported within the annular ring and the outer ring is disposed within the cavity of the instrument valve housing. The flap portions of the guard members of the guard assembly are configured to engage and stretch the septum seal during reception of a surgical instrument through the valve assembly.

In embodiments, the guard assembly includes first, second, third and fourth guard members. Each of the guard members may include a ring portion and a flap portion. The flap portions may not extend beyond a midline of the ring portions. The first and second flap portions may be disposed opposite one another, and the third and fourth flap portions may be disposed opposite one another. The first and second flap portions may be disposed perpendicular to the third and fourth flap portions. The flap portions may include a substantial mushroom cap shape.

The guard assembly of the valve assembly may further include upper and lower retainer members. At least one of the upper or lower retainer members may include a plurality of pins configured to engage the ring portions of the plurality of guard members. The flap portion of the first guard member may overlap the flap portion of the second guard member. The flap portion of the second guard member may overlap the flap portion of the third guard member. The flap portion of the third guard member may overlap the flap portion of the fourth guard member. The flap portion of the fourth guard member may overlap the flap portion of the first guard member.

Another cannula for use in an access assembly is provided. The cannula includes an instrument valve housing including first and second housing sections and defining a cavity, and a valve assembly disposed within the cavity of the instrument valve housing. The valve assembly includes a seal assembly including an outer flange and a septum seal extending across the outer flange, a guard assembly disposed within the outer flange of the seal assembly, and a centering mechanism including an annular ring and a plurality of spokes extending outwardly from the annular ring the guard assembly including a guard member having a ring portion and a plurality of petals. The outer flange of the seal assembly is supported within the annular ring. The plurality of petals of the guard member are configured to engage and stretch the septum seal during reception of a surgical instrument through the valve assembly.

In embodiments, each petal of the plurality of petals includes a flap portion and a connector portion. Each of the flap portions may be connected to the ring member by a respective connector portion. The plurality of petals may extend radially outward from the ring portion. The plurality of petals may be configured to be folded over the ring portion such that the flap portions overlap adjacent flap portions. Each of the flap portions may define one or more openings and the ring portion defines corresponding openings.

The guard assembly of the valve assembly may further include upper and lower retainer members. At least one of the upper or lower retainer members may include a plurality of pins. The one or more openings in the flap portions and the corresponding openings in the ring portion may be configured to receive the plurality of pins of the at least one upper or lower retainer members.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Figure 1:
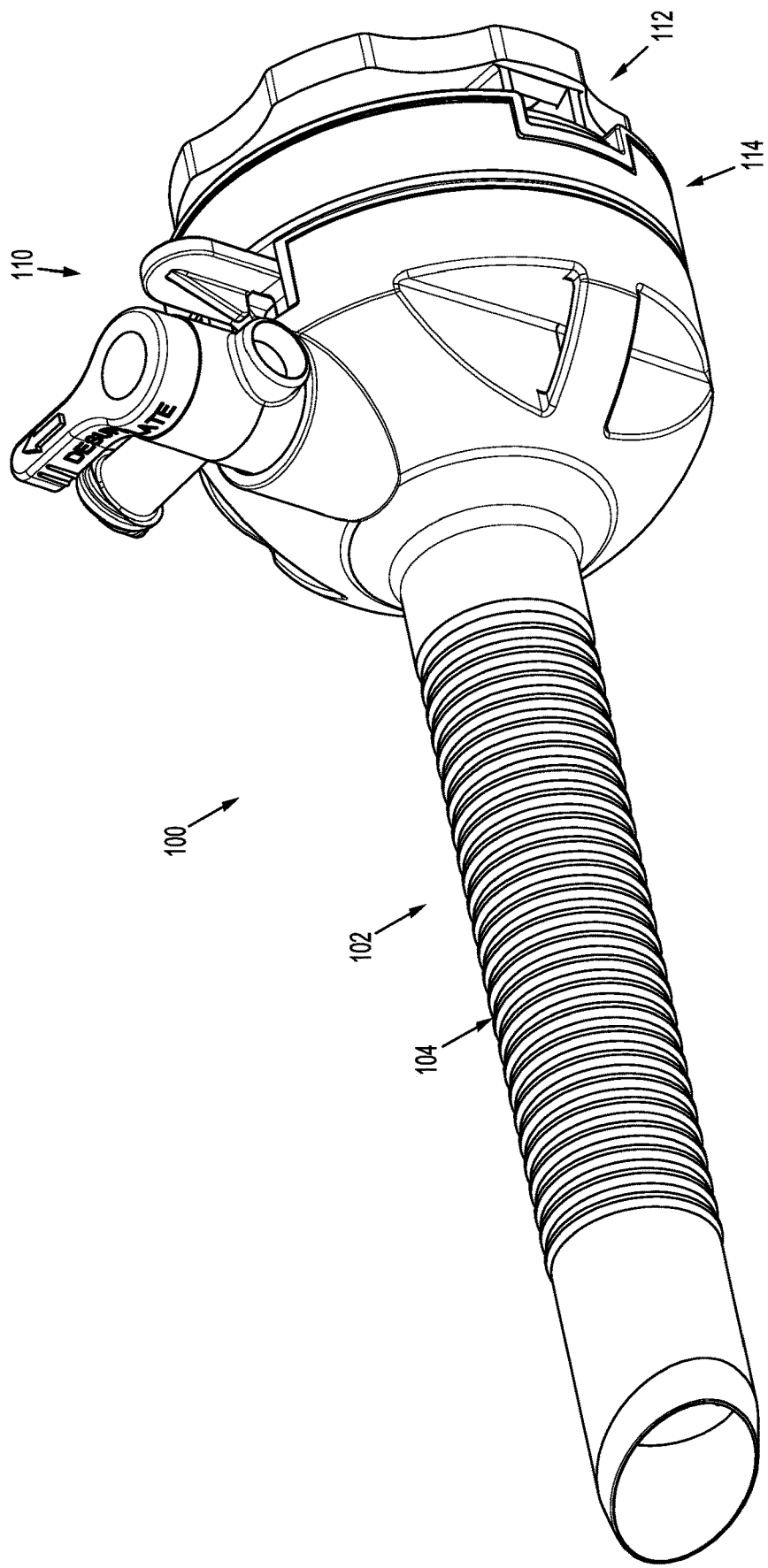
FIG. 1 is a perspective side view of a cannula of a trocar assembly according to an embodiment of the present disclosure.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user.

Cannulas are employed during, e.g., laparoscopic surgery and may, in various embodiments, provide for the sealed access of laparoscopic surgical instruments into an insufflated body cavity, such as the abdominal cavity. The cannulas of the present disclosure include an instrument valve housing mounted on a cannula tube. Cannulas are typically part of a trocar assembly including a trocar obturator. The trocar obturator is insertable through the cannula to facilitate placement of the cannula through tissue. The cannula and the trocar obturator are separate components but are capable of being selectively connected together. For example, the trocar obturator may be inserted into and through the cannula until the handle of the trocar obturator engages, e.g., selectively locks into, the instrument valve housing of the cannula.

Trocar assemblies are employed to tunnel through an anatomical structure, e.g., the abdominal wall, either by making a new passage through the structure or by passing through an existing opening through the structure. Once the trocar assembly has tunneled through the anatomical structure, the trocar obturator is removed, leaving the cannula in place in the structure, e.g., in the incision created by the trocar assembly. The instrument valve housing of the cannula may include valves that prevent the escape of insufflation gases from the body cavity, while also allowing surgical instruments to be inserted into the cavity.

In various embodiments, a bladeless optical trocar obturator may be provided that permits separation of tissue planes in a surgical procedure and visualization of body tissue fibers as they are being separated, thereby permitting a controlled traversal across a body wall. In other embodiments, the trocar obturator may be bladeless without being optical, e.g., without providing contemporaneous visualization thereof through the distal tip of an obturator. The bladeless obturator may be provided for the blunt dissection of the abdominal lining during a surgical procedure.

Various trocar obturators suitable for use with the cannulas of the present disclosure are known and include, for example, bladed, bladeless, blunt, optical, non-optical. The trocar assemblies will only be described to the extent necessary to disclose the aspects of the present disclosure. For a detailed description of the structure and function of exemplary trocar assemblies, including exemplar trocar obturators and exemplar cannulas, please refer to commonly owned PCT Publication No WO 2016/186905 ("the '905 publication"), the content of which is hereby incorporated by reference herein in its entirety.

With initial reference now to FIG. 1, a cannula according to aspects of the present disclosure is shown generally as cannula 100. The cannula 100 includes a cannula assembly 102 and an instrument valve housing 110 secured to the cannula assembly 102. The cannula assembly 102 will only be described to the extent necessary to fully disclose the aspects of the present disclosure. For a detailed description of an exemplary cannula assembly, please refer to the '905 publication.

Figures 2, 3:
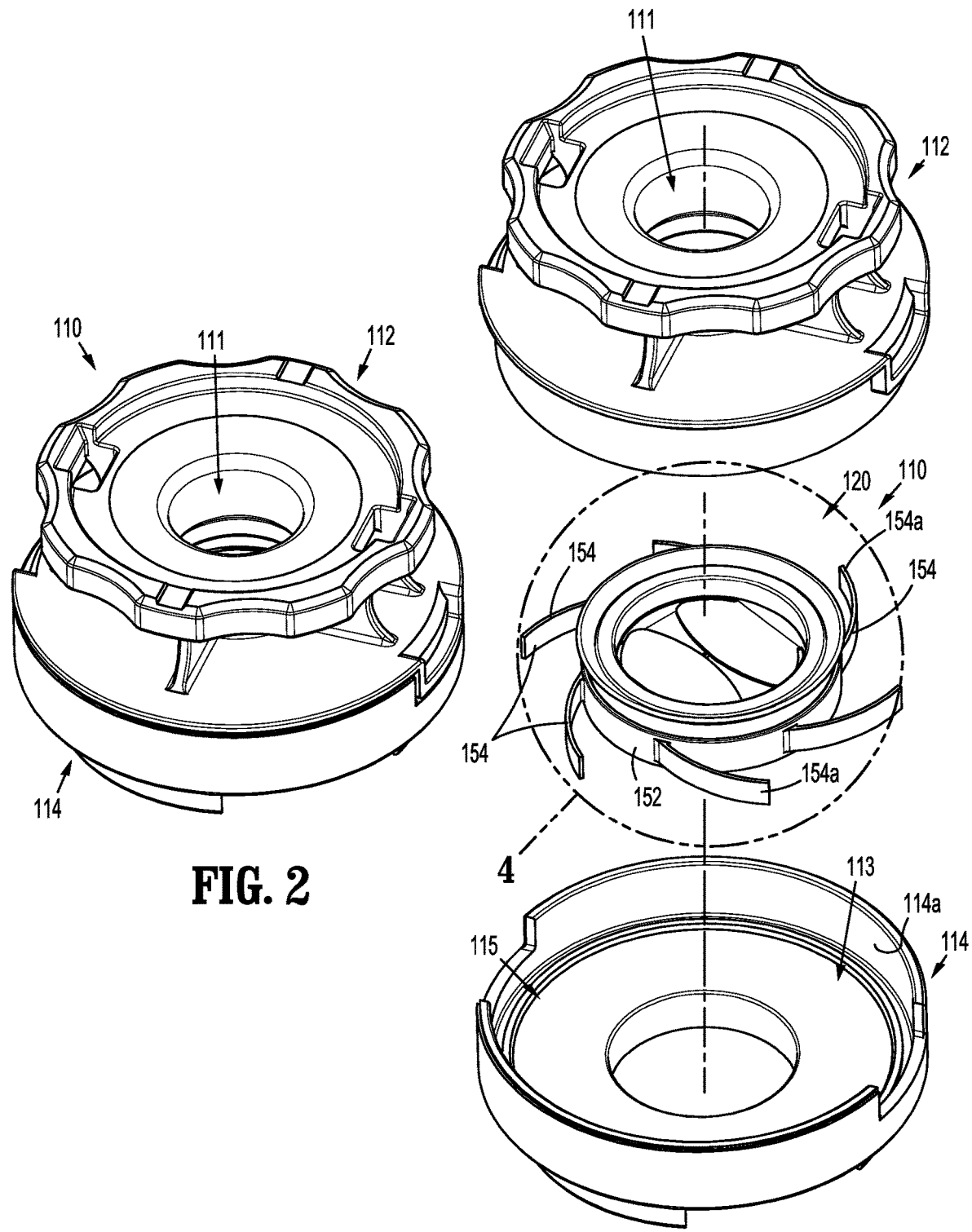
FIG. 2 is a perspective top view of an instrument valve housing of the cannula shown in FIG. 1.
FIG. 3 is an exploded top view of the instrument valve housing shown in FIG. 2, including first and second housing sections, separated, and a valve assembly.

With reference to FIGS. 2 and 3, the instrument valve housing 110 of the cannula 100 includes a first housing section 112 and a second housing section 114. The first and second housing section 112, 114 are configured to support a valve assembly 120 on a proximal end of the cannula assembly 102. More particularly, the first and second housing sections 112, 114 define a cavity 113 for operably receiving the valve assembly 120. The first housing section 112 of the instrument valve housing 110 may be selectively attachable to, and detachable from, the second housing section 114. The second housing section 114 may be releasably or permanently attached to a cannula tube 104 of the cannula assembly 102. In embodiments, either or both of the first and second housing sections 112, 114 of the instrument valve housing 110 may include knurls, indentations, tabs, or be otherwise configured to facilitate engagement by a clinician.

The first and second housing sections 112, 114 of the instrument valve housing 110 define a longitudinal passage 111 for receipt of a surgical instrument (not shown). The valve assembly 120 is supported within the first and second housing sections 112, 114 to provide sealed passage of the surgical instrument through the instrument valve housing 110.

Figure 4:
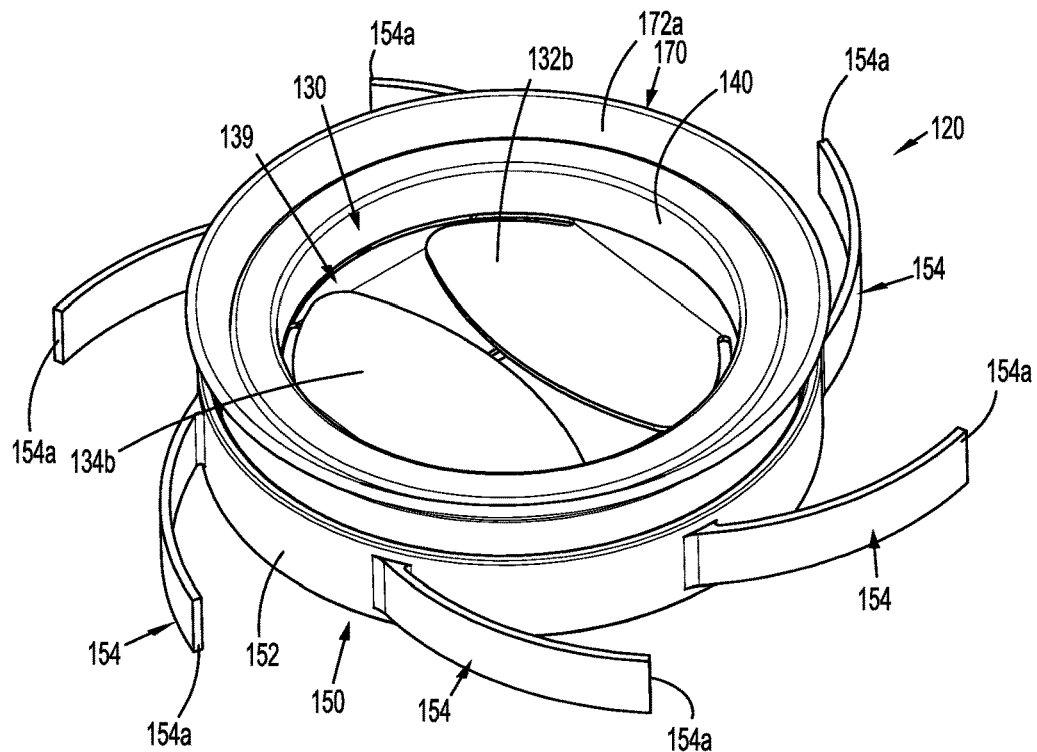
FIG. 4 is a perspective top view of the valve assembly shown in FIG. 3.
Figure 5:
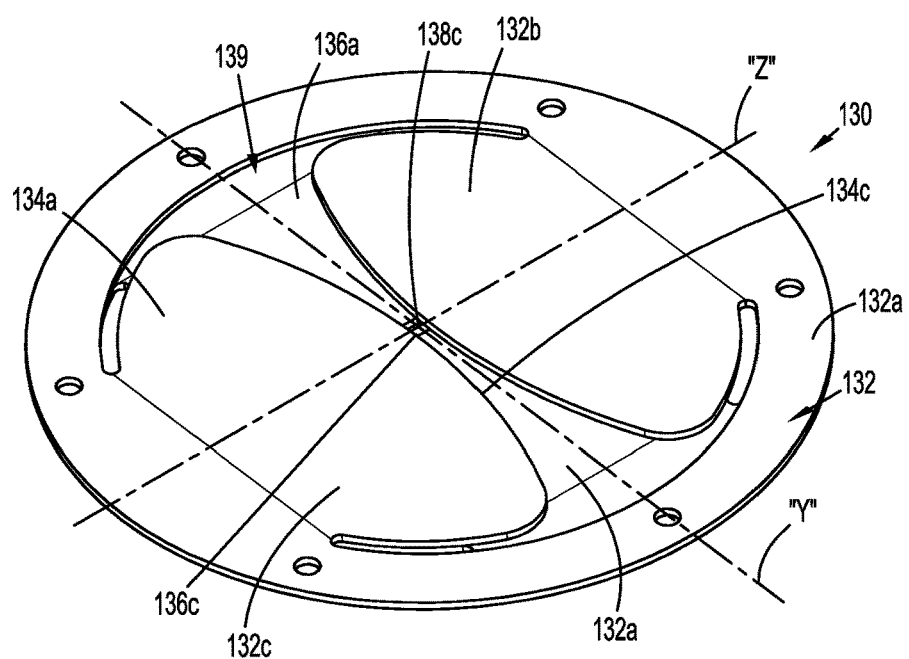
FIG. 5 is a perspective top view of a plurality of guard members of a guard assembly of the valve assembly shown in FIG. 3.
Figure 6:
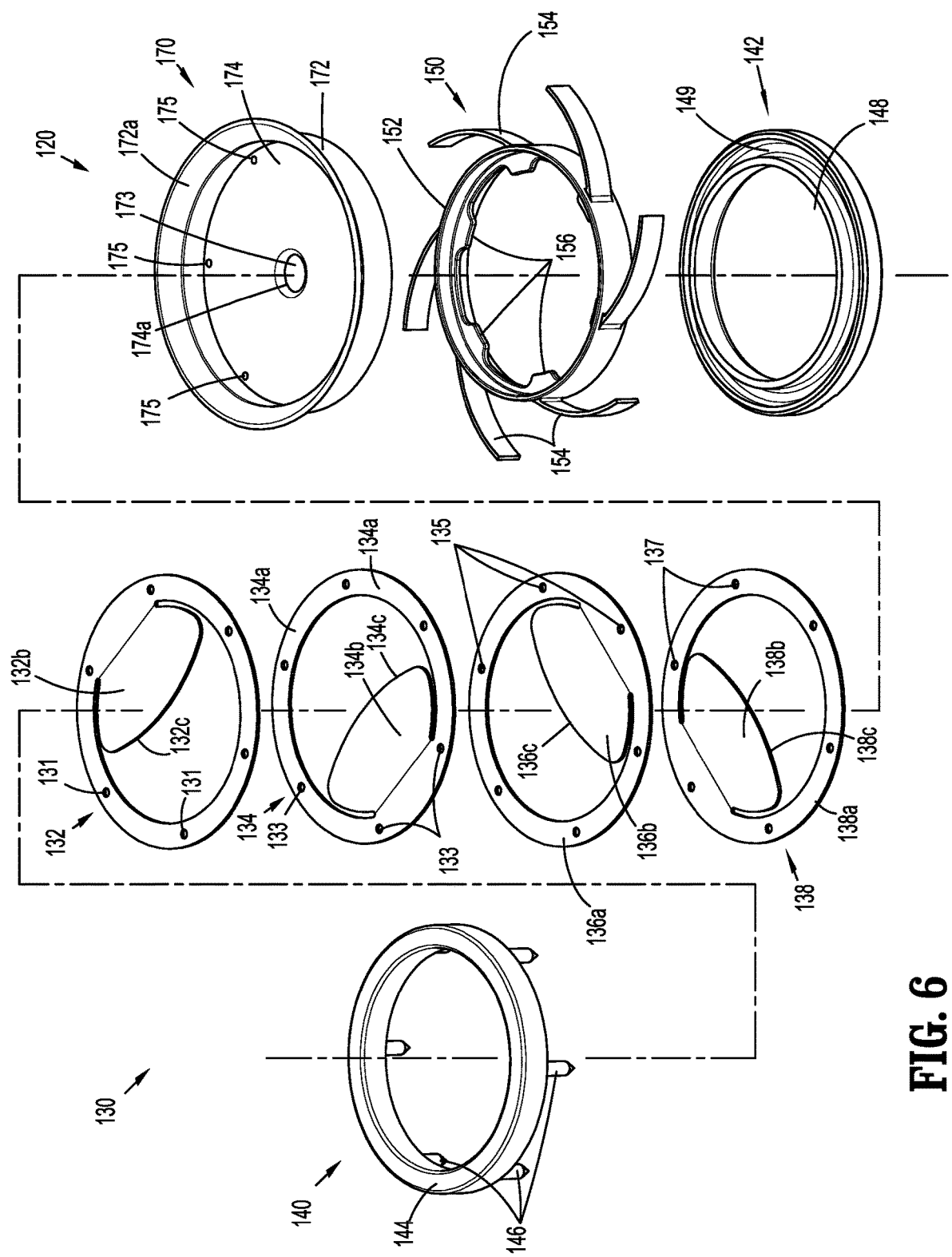
FIG. 6 is an exploded view of the valve assembly shown in FIG. 3, with parts separated.

With particular reference to FIGS. 4-6, the valve assembly 120 supported in the instrument valve housing 110 includes a guard assembly 130, a centering mechanism 150, and a seal assembly 170. As will be described in further detail below, the guard assembly 130 is configured to protect the seal assembly 170 during insertion and withdrawal of a surgical instrument through the seal assembly 170. The centering mechanism 150 is configured to permit radial movement of the valve assembly 120 relative to the instrument valve housing 110 when a surgical instrument is received through the valve assembly 120, and returns the valve assembly 120 to a centered position once the surgical instrument is withdrawn from within the instrument valve housing 120. The seal assembly 170 provides sealed passage of the surgical instrument through the instrument valve housing 110.

The guard assembly 130 of the valve assembly 120 supported within the instrument valve housing 110 includes first, second, third, and fourth guard members 132, 134, 136, 138. The guard members 132, 134, 136, 138 are formed of rigid plastic or other suitable material. Each of the first, second, third, and fourth guard members 132, 134, 136, 138 includes a ring portion 132a, 134a, 136a, 138a and a flap portion 132b, 134b, 136b, 138b. The ring portions 132a, 134a, 136a, 138a of the first, second, third, and fourth guard members 132, 134, 136, 138 each define a plurality of openings 131, 133, 135, 137, respectively. Each opening of the plurality of openings 131, 133, 135, 137 is configured to receive a pin of a plurality of pins 146 of an upper retainer member 140.

Each of the flap portions 132b, 134b, 136b, 138b of the respective first, second, third, and fourth guard members 132, 134, 136, 138 of the guard assembly 130 extends radially inward from the ring portions 132a, 134a, 136a, 138a. Each of the flap portions 132b, 134b, 136b, 138b includes a substantial mushroom cap shape having a curved outer edge 132c, 134c, 136c, 138c. The flap portions 132b, 134b, 136b, 138b do not extend beyond a midline of the respective first, second, third, and fourth guard members 132, 134, 136, 138, e.g., midline "y" of the first and second guard members 132, 134 and midline "z" of the third and fourth guard members 136, 138, shown in FIG. 5).

As shown in FIGS. 5 and 6, the first, second, third, and fourth guard members 132, 134, 136, 138 are arranged one on top of another, e.g., stacked configuration. As shown, the first and second guard members 132, 134 are arranged such that the respective flap portions 132b, 134b are opposed to one another and do not overlap. The first and second flap portions 132b, 134b form a first layer occupying a majority of the opening 139 defined by the ring portions 132a, 134a of the respective first and second guard members 132, 134. Similarly, the third and fourth guard members 136, 138 are arranged such that the respective flap portions 136b, 138b are opposed to one another and do not overlap. The third and fourth flap portions 136b, 138b of the third and fourth guard members 136, 138 form a second layer occupying a majority of the opening 139 defined by the ring portions 136a, 138a of the respective third and fourth guard members 136, 138.

As shown in FIG. 5, are offset by ninety degrees (90°) relative to each other. In this manner, first and second guard members 132, 134 are perpendicular to the third and fourth guard members 136, 138, and together, occupy nearly the entire opening 139 defined by the ring portions 132a, 134a, 136a, 138a. The flap portions 132b, 134b, 136b, 138b of the respective first, second, third and fourth guard members 132, 134, 136, 138 are configured to flex downward upon engagement with a surgical instrument to facilitate passage of the surgical instrument through seal assembly 170. More particularly, engagement of the first and second flap portions 132b, 134b of the first and second guard members 132, 134, respectively, flexes the first and second flap portions 132b, 134b downward into engagement with the third and fourth flap portions 136b, 138b of the third and fourth guard members 136, 138. Continued insertion of the surgical instrument through the guard assembly 130 causes each of the first, second, third, and fourth flap portions 132b, 134b, 136b, 138b to engage with a septum seal 174 of the seal assembly 170 to stretch the septum seal 174 of the seal assembly 170 to increase the size of a central opening 173 of the septum seal 174. The increased size of the central opening 173 the septum seal 174 permits receipt of the surgical instrument through the valve assembly 120. The larger the diameter of the surgical instrument, the more the first, second, third, and fourth flap portions 132b, 134b, 136b, 138b of the first, second, third, and fourth guard members 132, 134, 136, 138 are flexed downward and the greater the size of the central opening 173 in the septum seal 174. The flap portions 132b, 134b, 136b, 138b guide and center the surgical instrument through the septum seal 174. In addition, the flap portions 132b, 134b, 136b, 138b may also inhibit inversion of the seal assembly 170 during withdrawal of a surgical instrument from the seal assembly 170.

It is envisioned that the guard assembly 130 may include a guard member (not shown) including a pair of opposed flap portions (not shown) supported on a single ring portion. In embodiments, the flap portions may extend radially outward from the ring portions, thereby necessitating folding the flap portions over the ring portions. See, for example, the embodiment of FIG. 8. The guard assembly may include any number of guard members, and the guard members may include flap portions of any size or configuration.

Figure 7:
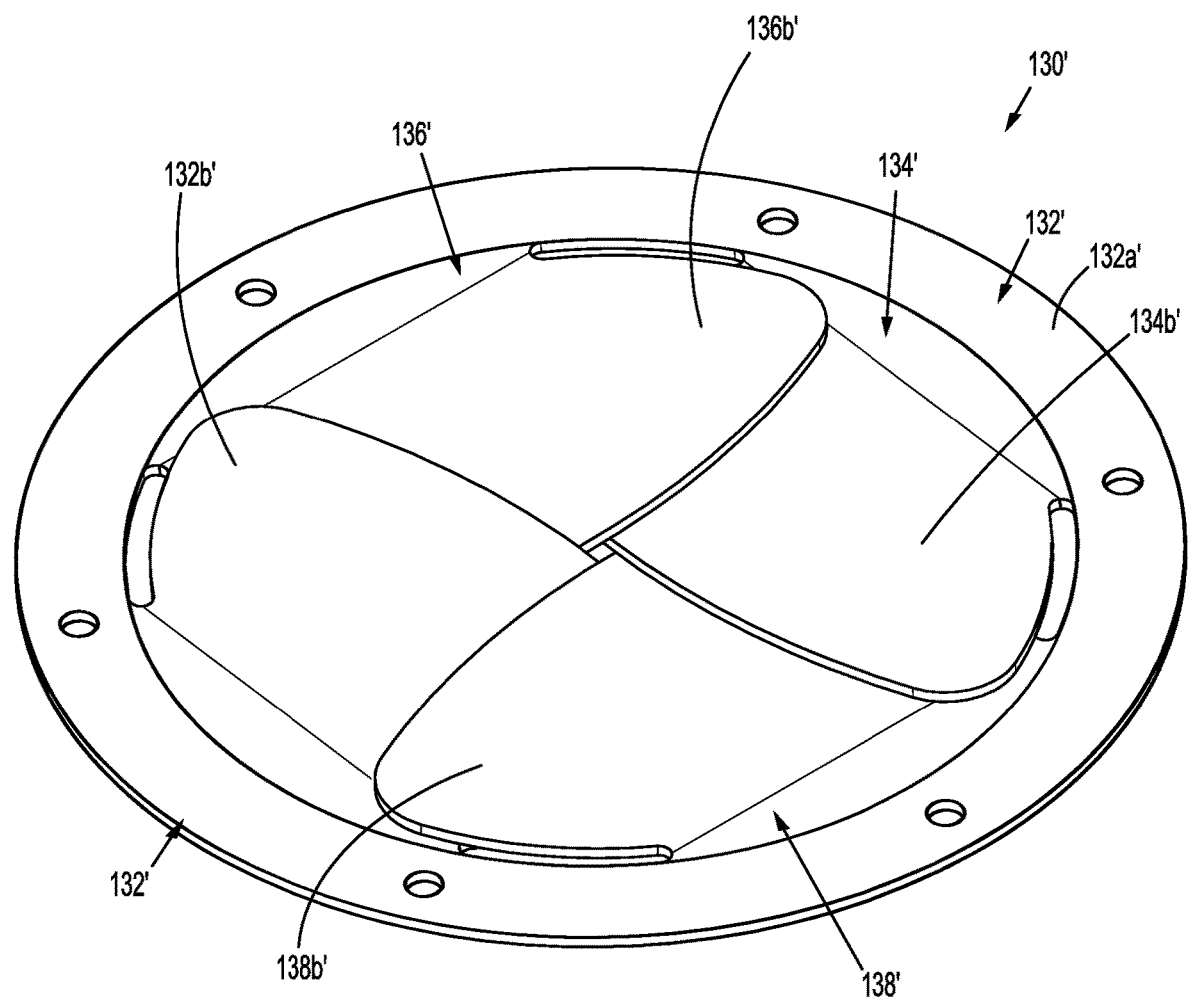
FIG. 7 is a perspective top view of the plurality of guard members of the guard assembly shown in FIG. 3, with the guard members in an alternative configuration.

Turning briefly to FIG. 7, in an alternative embodiment of the guard assembly 130', the flap portions 132b', 134b', 136b', 138b' of the respective first, second, third and fourth guard members 132', 134', 136', 138' overlap with one another. More particularly, the first flap portion 132b' of the first guard member 132' overlaps the third flap portion 136b' of the third guard member 136', the third flap portion 136b' of the third guard member 136 overlaps the second flap portion 134b' of the second guard member 134', the second flap portion 134b' of the second guard member 134' overlaps the fourth flap portion 138b of the fourth guard member 138', and the fourth flap portion 138b' of the fourth guard member 138 overlaps the first flap portion 132b' of the first guard member 132'.

With reference again to FIG. 6, the guard assembly 130 further includes upper and lower retainer members 140, 142 for retaining the first, second, third and fourth guard members 132, 134, 136, 138. More particularly, the upper retainer member 140 includes a base 144 and the plurality of fingers or pins 146 extending downwardly from the base 144. The lower retainer member 142 includes a base 148 defining an annular channel 149 for securely receiving the plurality of pins 146 of the upper retainer member 140.

Although the plurality of pins 146 is shown as extending downwardly from the base 144 of the upper retainer member 140 for engagement with the lower retainer member 142, in other embodiments, the plurality of pins 146 may instead extend upwardly from the base 148 of the lower retainer member 142 for engagement with the upper retainer member 140, or the pins 146 may extend from both the upper and lower retainer members 140, 142 and extend both upwardly and downwardly. In addition, while the lower retainer member 142 is shown and described as including the annular channel 149, the lower retainer member 142 may instead include one or more discrete openings (not shown) for receiving the corresponding fingers or pins, which may improve the engagement of the pins 146 with the lower retainer member 142 and increase the retention between the pins 146 and the lower retainer member 142 once the upper and lower retainer members 140, 142 are connected to each other. Employing the channel 149 instead of the discrete openings eliminates the need to circumferential align the upper and lower retainer members 140, 142 prior to connecting the upper and lower retainer members 140, 142 to one another.

The plurality of pins 146 of the upper retainer member 140 of the guard assembly 130 are configured to be received through the plurality of openings 131, 133, 135, 137 in the respective ring portions 132a, 134a, 136a, 138a of the first, second, third, and fourth guard members 132, 134, 136, 138, respectively. Receipt of the plurality of pins 146 of the upper retainer member 140 of the guard assembly 130 through the plurality of openings 131, 133, 135, 137 in the respective first, second, third, and fourth guard members 132, 134, 136, 138 and subsequent attachment of the lower retainer member 142 to the upper retainer member 140 secures the first, second, third, and fourth guard members 132, 134, 136, 138 relative to one another. The upper and lower retainer members 140, 142 of the guard assembly 130 also secure the guard assembly 130 and seal assembly 170 the centering mechanism 150.

With particular reference to FIGS. 4 and 6, the centering mechanism 150 of the instrument valve housing 110 is configured to maintain the valve assembly 110 centered within the cavity 113 of the first and second housing sections 112, 114 of the instrument valve housing 110 (FIG. 3). More particularly, the centering mechanism 150 includes an annular ring 152 and a plurality of spokes or spring elements 154 extending radially outward from the annular ring 152. The centering mechanism 150 further includes a plurality of tabs 156 that extend inwardly from the annular ring 152 and are configured to engage the seal member 170. For a detailed description of the structure and function of an exemplary centering mechanism, please refer to commonly owned U.S. Pat. App. Pub. No. 2015/0025477 ("the '477 publication"), the content of which is incorporated herein by reference in its entirety. It is envisioned that the centering mechanism 150 may include two centering mechanisms, as disclosed in the '477 publication.

As described in the '477 publication, the plurality of spokes 154 of the centering mechanism 150 each include a free end 154a configured to engage an inner wall 114a (FIG. 3) of the lower housing section 114 when the valve assembly 120 is moved off-center to bias the valve assembly 120 back to a centered position.

Alternatively, the centering mechanism may include a bellows or otherwise be configured to maintain the valve assembly 120 centered within the instrument valve housing 110.

Referring again to FIG. 6, the seal member 170 of the valve assembly 120 is configured to provide a seal around an outer surface of a surgical instrument passing through the instrument valve housing 110. The seal member 170 includes an annular flange 172, and the septum seal 174 supported by the annular flange 172. As shown, a free end 172a of the annular flange 172 may extend radially outwardly and in a proximal direction to facilitate reception of a surgical instrument through the septum seal 174.

The septum seal 174 of the seal member 170 is formed of an elastic material, e.g., rubber, and defines a central opening 173. In embodiments, the septum seal 174 may include one or more fabric layers. The septum seal 174 is configured to provide a seal around an outer surface of a surgical instrument passing through the valve assembly 120. A surface 174a of the septum seal 174 defining the central opening 173 may be beveled or otherwise configured to facilitate reception of the surgical instrument through the central opening 173 in the septum seal 174. The septum seal 174 further defines a plurality of openings 175 corresponding to the pins 146 extending from the upper retainer member 140 of the guard assembly 130.

With particular reference to FIG. 4, the upper retainer member 140 of the guard assembly 130 of the valve assembly 120 is received within the annular flange 172 of the seal member 170 such that the pins 146 of the upper retainer member 140 are received through the openings 175 (FIG. 6) in the septum seal 174 of the seal member 170. Prior to receiving the pins 146 of the upper retainer member 140 through the openings 175 in the septum seal 174, the first, second, third and fourth guard members 132, 134, 136, 138 of the guard assembly 130 are secured to the upper retainer member 140. In this manner, when the pins 146 of the upper retainer member 140 are received through the openings 175 in the septum seal 174, the first, second, third, and fourth guard members 132, 134, 136, 138 of the guard assembly 130 are disposed within the annular flange 172 of the seal assembly 170. The lower retainer member 142 of the guard assembly 130 is secured to the upper retainer member 140 to secure the first, second, third, and fourth guard members 132, 134, 136, 138 relative to the seal assembly 170. The upper and lower retainer members 140, 142 also maintain alignment and orientation of the first, second, third, and fourth guard members 132, 134, 136, 138.

In an assembled configuration, the seal assembly 170, including the guard assembly 130, is received within the annular ring 152 of the centering mechanism 150. More particularly, the tabs 156 (FIG. 6) extending inwardly from the annular ring 152 of the center mechanism 150 engage an outer surface of the annular flange 172 to maintain the seal assembly 170 within the centering mechanism 150.

During a surgical procedure utilizing cannula 100, an instrument (not shown) is introduced into the instrument valve housing 110 through the longitudinal passage 113 in the first and second housing sections 112, 114. As described above, the distal end of the instrument engages the first and second flap portions 132b, 134b of the respective first and second guard members 132, 134. The first and second flap portions 132b, 134b flex downward into contact with the third and fourth flap portions 136b, 138b of the respective third and fourth guard members 136, 138. The first, second, third and fourth flap portions 132b, 134b, 136b, 138b flex into contact with the septum seal 174 of the seal member 170 to cause the central opening 173 of the septum seal 174 to open to accommodate passage of the surgical instrument through the septum seal 174. The first, second, third, and fourth guard members 132, 134, 136, 138 of the guard assembly 130 minimize damage to the seal member 170 during insertion of an instrument through the valve assembly 120.

The first, second, third, and fourth guard members 132, 134, 136, 138 of the guard assembly 130 operate to protect the septum seal 174 of the seal assembly 170 from tearing or other damage as a surgical instrument is received through the seal assembly 170. Additionally, the guard assembly 130 may prevent inversion of the septum seal 174 as the surgical instrument is retracted through the septum seal 174.

Figure 8:
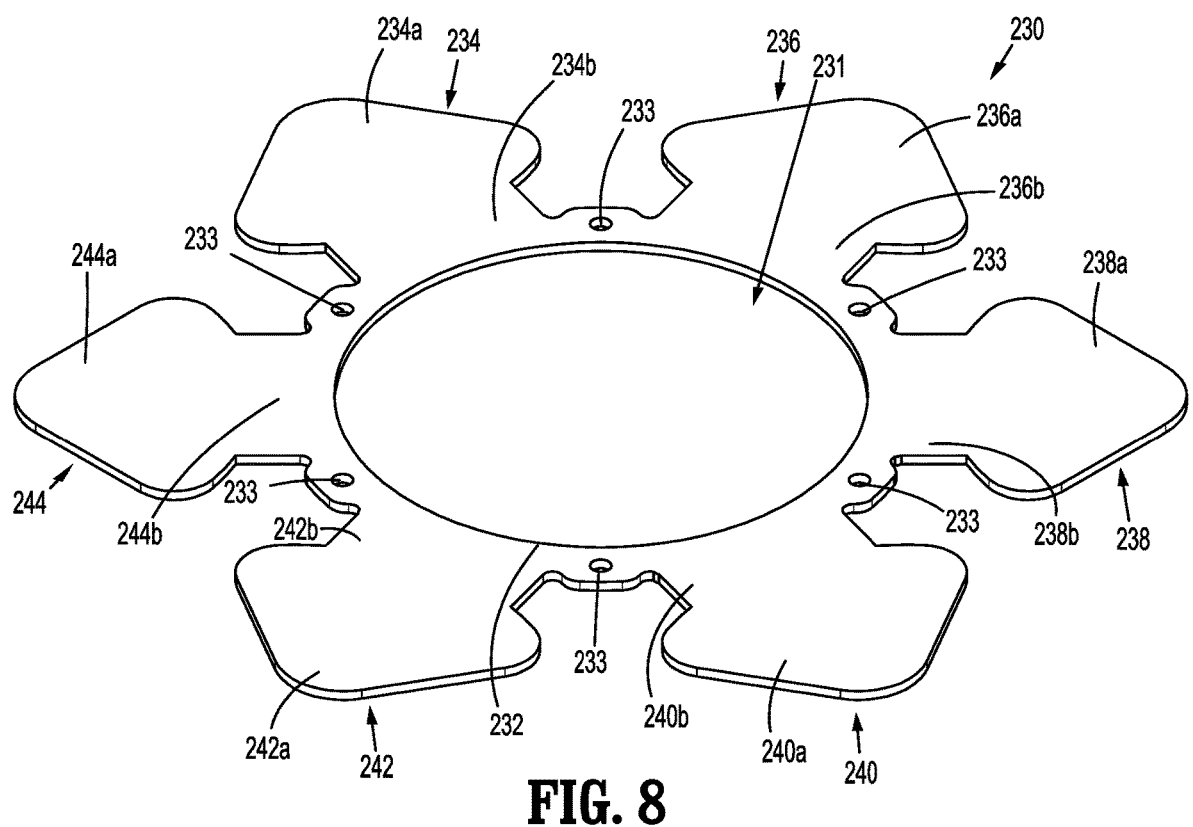
FIG. 8 is a perspective top view of a guard member according to another embodiment of the present disclosure, in an initial or pre-folded configuration.
Figure 9:
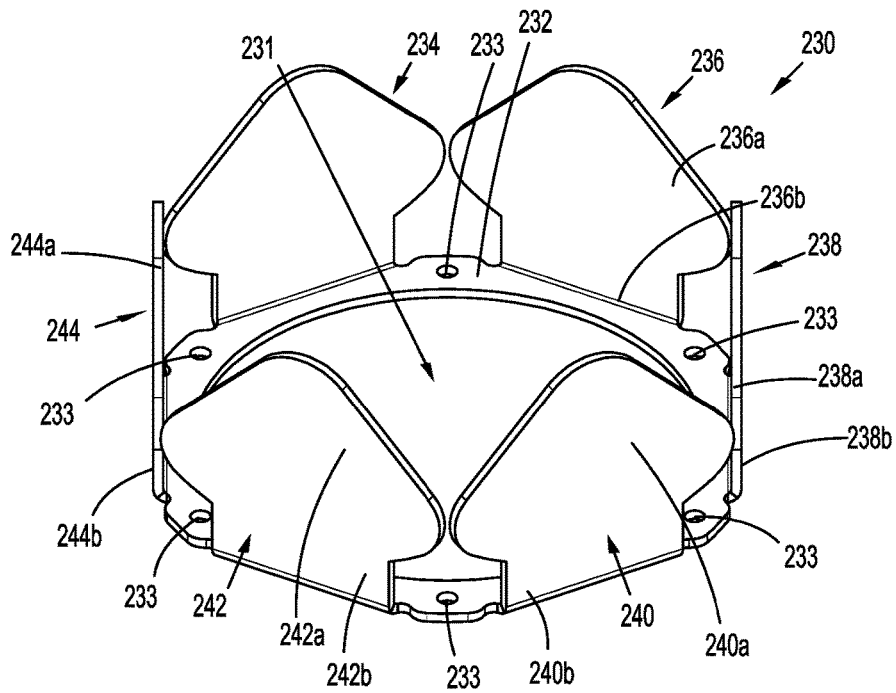
FIG. 9 is a perspective top view of the guard member shown in FIG. 8, in a second or partially-folded configuration.
Figure 10:
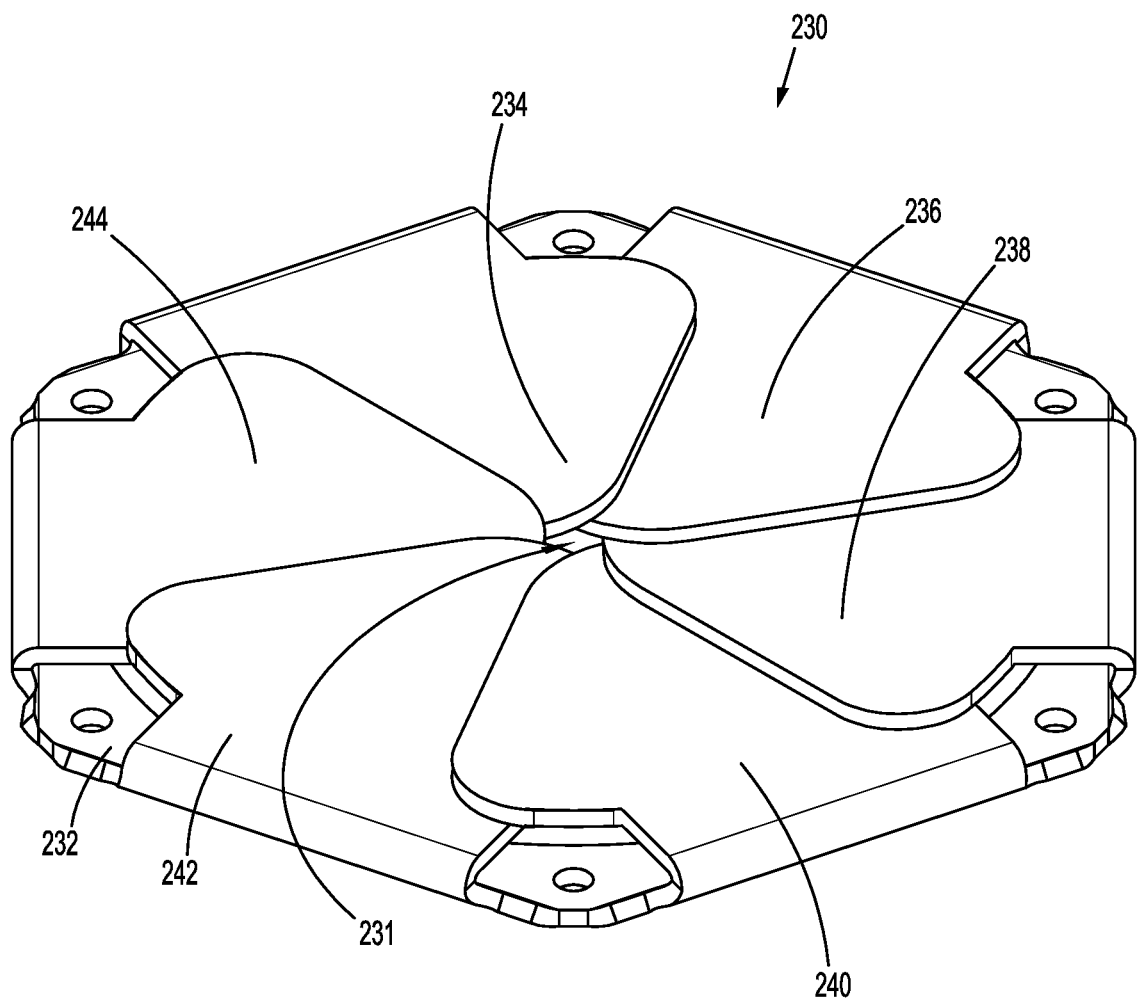
FIG. 10 is a perspective top view of the guard member shown in FIG. 8, in a fully-folded configuration.

With reference now to FIGS. 8-10, a guard member according to another embodiment of the present disclosure is shown generally as guard member 230. The guard member 230 includes a ring portion 232 and first, second, third, fourth, fifth, and sixth petals 234, 236, 238, 240, 242, 244 supported by and extending radially outward from the ring portion 232 when the guard member 230 is in an initial or pre-folded condition (FIG. 8).

The ring portion 232 of the guard member 230 defines a plurality of openings 233 to facilitate engagement of the guard member 230 by retainer members, e.g., the upper and lower retainer members 140, 142 (FIG. 6). The ring portion 232 may define one or more openings corresponding to the first, second, third, fourth, fifth, and sixth petals 234, 236, 238, 240, 242, 244. In embodiments, and as will be described in further detail below, the plurality of petals may also each define one or more openings (FIG. 12) corresponding to openings in the ring portions when the petals are in a fully-folded condition (FIG. 10).

Each of the first, second, third, fourth, fifth, and sixth petals 234, 236, 238, 240, 242, 244 of the guard member 230 includes a flap portion 234a, 236a, 238a, 240a, 242a, 244a and a connector portion 234b, 236b, 238b, 240b, 242b, 244b connecting the flap portions 234a, 236a, 238a, 240a, 242a, 244a of the respective first, second, third, fourth, fifth, and sixth petals 234, 236, 238, 240, 242, 244 to the ring portion 232. In embodiments, and as shown, the flap portions 234a, 236a, 238a, 240a, 242a, 244a of the first, second, third, fourth, fifth, and sixth petals 234, 236, 238, 240, 242, 244, respectively, define a spade-like body, although other configurations are envisioned. Similarly, although shown having six (6) petals, it is envisioned that the guard member may have more or less than six (6) petals.

The connector portions 234b, 236b, 238b, 240b, 242b, 244b of the respective petals 234, 236, 238, 240, 242, 244 are configured to permit inward folding of the respective petals 234, 236, 238, 240, 242, 244 such that the flap portions 234a, 236a, 238a, 240a, 242a, 244a of the respective first, second, third, fourth, fifth, and sixth petals 234, 236, 238, 240, 242, 244 occupy substantially the entire opening 231 defined by the ring portion 232. In embodiments, and as shown, the first, second, third, fourth, fifth, and sixth petals 234, 236, 238, 240, 242, 244 are configured to overlap one another when folded, as described below. The connector portions 234b, 236b, 238b, 240b, 242b, 244b may provide increased stability and structure to the respective first, second, third, fourth, fifth, and sixth petals 234, 236, 238, 240, 242, 244.

Figure 11:
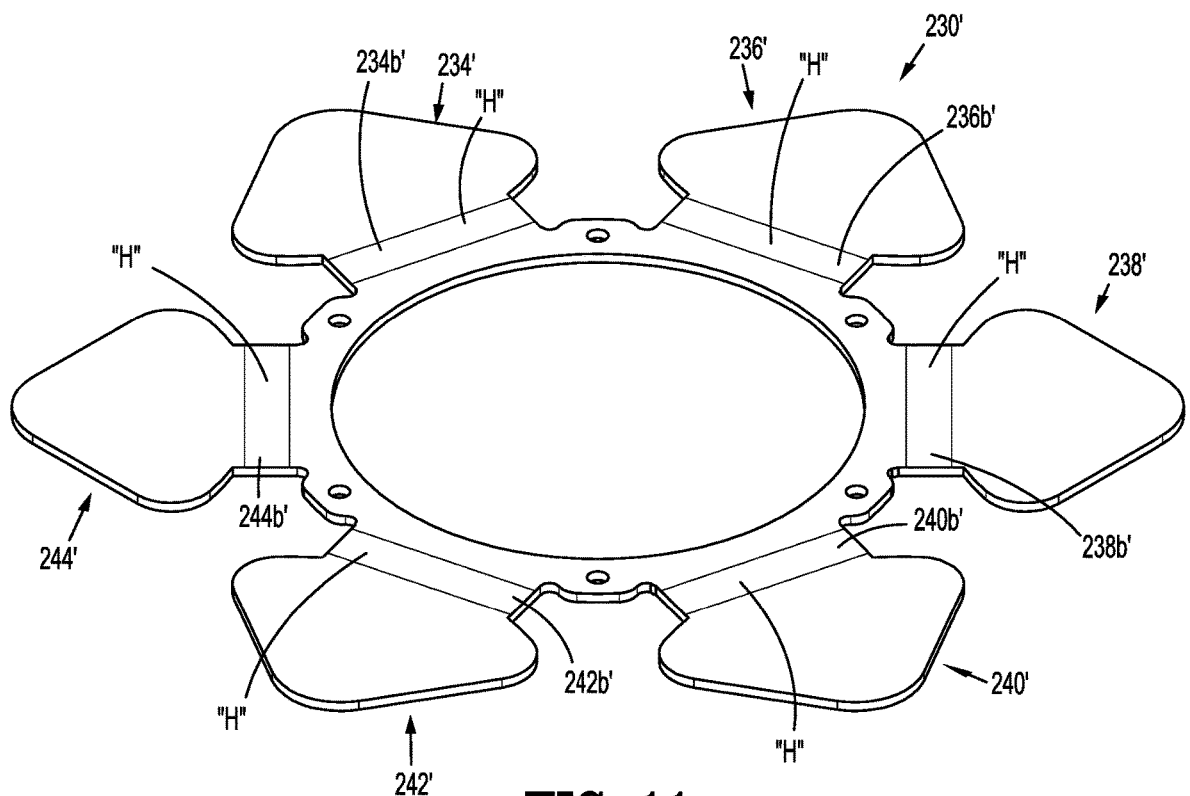
FIG. 11 is a perspective top view of a guard member according to yet another embodiment of the present disclosure.

Turning briefly to FIG. 11, in embodiments, connector portions 234b', 236b', 238b', 240b', 242b', 244b' of respective first, second, third, fourth, fifth, and sixth petals 234', 236', 238', 240', 242', 244' of a guard member 230' define a hinge feature "H" to facilitate folding of the respective first, second, third, fourth, fifth, and sixth petals 234', 236', 238', 240', 242', 244'. The hinge feature "H" may be a living hinge including a weakened or thinned portion of the connector portions 234b', 236b', 238b', 240b', 242b', 244b'. The hinge feature "H" may also facilitate orienting and aligning the first, second, third, fourth, fifth, and sixth petals 234', 236', 238', 240', 242', 244'.

With particular reference to FIG. 10, the first, second, third, fourth, fifth, and sixth petals 234, 236, 238, 240, 242, 244 of the guard member 230 are shown in a sequentially overlapping configuration. More particularly, the flap portion 234a of the first petal 234 overlaps the flap portion 236a of the second petal 236, which overlaps the flap portion 238a of the third petal 238, which overlaps the flap portion 240a of the fourth petal 240, which overlaps the flap portions 242a of the fifth petal 242, which overlaps the flap portion 244a of the sixth petal 244. In this manner, downward flexing of one of the flap portions 234, 236, 238, 240, 242, 244 during engagement by a surgical instrument causes downward flexing of all of the flap portions 234, 236, 238, 240, 242, 244.

Alternatively, the first, second, third, fourth, fifth, and sixth petals 234, 236, 238, 240, 242, 244 of the guard member 230 may be arranged in an alternating pattern. More particularly, the first, second, third, fourth, fifth, and sixth petals 234, 236, 238, 240, 242, 244 are arranged such that the second and sixth petals 236, 244 overlap the first petal 234, the second and fourth petals 236, 240 overlap the third petal 238, and the fourth and sixth petals 240, 244 overlap the fifth petal 242.

Figure 12:
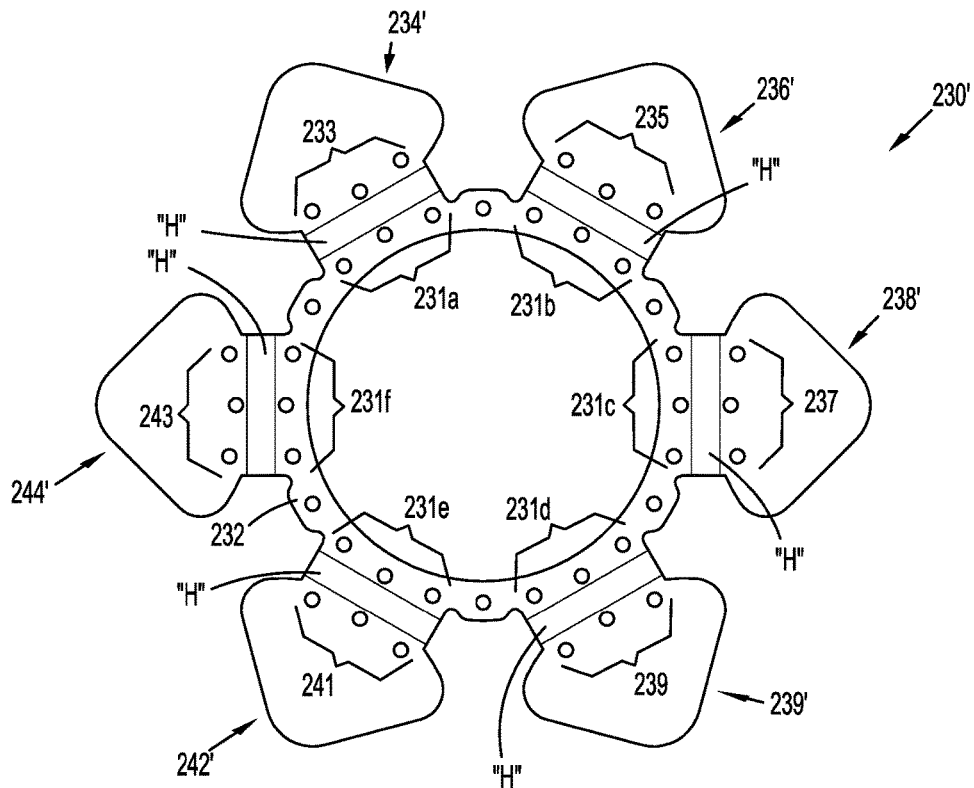
FIG. 12 is a top view of a guard member according to still another embodiment of the present disclosure.

With reference to FIG. 12, in an alternative embodiment, a guard assembly 230' includes a ring portion 232' and first, second, third, fourth, fifth, and sixth petals 234', 236', 238', 240', 242', 244' each including a respective flap portion 234a', 236a', 238a', 240a', 242a', 244a'. Each of the flap portions 234a', 236a', 238a', 240a', 242a', 244a' defines one or more openings 233, 235, 237, 239, 241, 243 corresponding to one or more openings 231a, 231b, 231c, 231d, 231e, 231f in the ring portion 232'. The one or more openings 233, 235, 237, 239, 241, 243 of the respective of the flap portions 234a', 236a', 238a', 240a', 242a', 244a align with the corresponding one or more openings 231a, 231b, 231c, 231d, 231e, 231f in the ring portion 232' when the first, second, third, fourth, fifth, and sixth petals 234', 236', 238', 240', 242', 244' are in a folded configuration, e.g., FIG. 10.

The one or more openings 233, 235, 237, 239, 241, 243 of the first, second, third, fourth, fifth, and sixth petals 234', 236', 238', 240', 242', 244' are configured to receive pins, e.g., pins 146 (FIG. 6) of a retainer member, e.g., upper retainer member 140. Receipt of the pins through the one or more openings 233, 235, 237, 239, 241, 243 align the first, second, third, fourth, fifth, and sixth petals 234, 236, 238, 240, 242, 244 relative to each other and provide structure support to the guard member 230'.

While various embodiments of the present disclosure have been shown and described herein, it will be obvious to those skilled in the art that these embodiments are provided by way of example only. Numerous variations, changes, and substitutions will now occur to those skilled in the art without departing from the present disclosure. Accordingly, it is intended that the invention be limited only by the spirit and scope of the appended claims.

The invention claimed is:

1. A valve assembly for a surgical access device, the valve assembly comprising:
   a seal assembly including an outer flange and a septum seal extending across the outer flange;
   a guard assembly disposed within the outer flange of the seal assembly, the guard assembly including a plurality of guard members, each guard member of the plurality of guard members consisting of a ring portion and a single flap portion extending from the ring portion; and
   a centering mechanism including an annular ring and a plurality of spokes extending outwardly from the annular ring, the outer flange of the seal assembly being supported within the annular ring, wherein the flap portions of the guard members of the guard assembly are configured to engage and stretch the septum seal during reception of a surgical instrument through the valve assembly.

2. The valve assembly of claim 1, wherein the guard assembly includes first, second, third and fourth guard members, each of the guard members including a ring portion and a single flap portion.

3. The valve assembly of claim 2, wherein the flap portions do not extend beyond a midline of the ring portions.

4. The valve assembly of claim 2, wherein the flap portions of the first and second guard members are disposed opposite one another and the flap portions of the third and fourth guard members are disposed opposite one another.

5. The valve assembly of claim 4, wherein the flap portions of the first and second guard members are disposed perpendicular to the flap portions of the third and fourth guard members.

6. The valve assembly of claim 2, wherein the flap portions include a substantial mushroom cap shape.

7. The valve assembly of claim 1, wherein the guard assembly further includes upper and lower retainer members, at least one of the upper or lower retainer members including a plurality of pins configured to engage the ring portions of the plurality of guard members.

8. The valve assembly of claim 2, wherein the flap portion of the first guard member overlaps the flap portion of the second guard member, the flap portion of the second guard member overlaps the flap portion of the third guard member, the flap portion of the third guard member overlaps the flap portion of the fourth guard member and the flap portion of the fourth guard member overlaps the flap portion of the first guard member.

9. A valve assembly comprising:
   a seal assembly including an outer flange and a septum seal extending across the outer flange;
   a guard assembly disposed within the outer flange of the seal assembly, the guard assembly including a guard member having a ring portion and a plurality of petals, each petal of the plurality of petals having an outwardly curved outer edge; and
   a centering mechanism including an annular ring and a plurality of spokes extending outwardly from the annular ring, the outer flange of the seal assembly being supported within the annular ring, wherein the plurality of petals of the guard member are configured to engage and stretch the septum seal during reception of a surgical instrument through the valve assembly.

10. The valve assembly of claim 9, wherein each petal of the plurality of petals includes a flap portion and a connector portion, each of the flap portions being connected to the ring member by a respective connector portion.

11. The valve assembly of claim 10, wherein the plurality of petals extends radially outward from the ring portion.

12. The valve assembly of claim 11, wherein the plurality of petals is configured to be folded over the ring portion such that the flap portions overlap adjacent flap portions.

13. The valve assembly of claim 10, wherein each of the flap portions defines one or more openings and the ring portion defines corresponding openings.

14. The valve assembly of claim 13, wherein the guard assembly further includes upper and lower retainer members, at least one of the upper or lower retainer members including a plurality of pins.

15. The valve assembly of claim 14, wherein the one or more openings in the flap portions and the corresponding openings in the ring portion are configured to receive the plurality of pins of the at least one upper or lower retainer members.

16. A valve assembly comprising:
    a seal assembly including an outer flange and a septum seal extending across the outer flange;
    a guard assembly disposed within the outer flange of the seal assembly, the guard assembly including a plurality of guard members, each guard member of the plurality of guard members having a ring portion and a flap portion, the flap portions having a substantially mushroom cap shape; and
    a centering mechanism including an annular ring and a plurality of spokes extending outwardly from the annular ring, the outer flange of the seal assembly being supported within the annular ring, wherein the flap portions of the plurality of guard members of the guard assembly are configured to engage and stretch the septum seal during reception of a surgical instrument through the valve assembly.

17. The valve assembly of claim 16, wherein the guard assembly includes first, second, third and fourth guard members, each of the guard members including a ring portion and a flap portion.

18. The valve assembly of claim 17, wherein the flap portions do not extend beyond a midline of the ring portions.

19. The valve assembly of claim 16, wherein the guard assembly further includes upper and lower retainer members, at least one of the upper or lower retainer members including a plurality of pins configured to engage the ring portions of the plurality of guard members.

* * * * *